United States Patent [19]
Hartmann

[11] Patent Number: 5,955,054
[45] Date of Patent: Sep. 21, 1999

[54] DIAGNOSTIC ASSAY FOR LOCALIZING *H. PYLORI*

[76] Inventor: John F. Hartmann, One Woodmeadow La., Princeton Junction, N.J. 08550-1323

[21] Appl. No.: 09/069,124

[22] Filed: Apr. 29, 1998

[51] Int. Cl.⁶ .......................... A61K 51/00; A61M 36/14
[52] U.S. Cl. ...................... 424/1.65; 424/1.11; 424/9.1; 424/9.4
[58] Field of Search ................. 424/1.11, 1.65, 424/9.1, 9.2, 9.3, 9.4, 9.5, 9.6, 9.7; 206/223, 569, 570; 430/944; 562/590, 584, 595; 549/315

[56] References Cited

U.S. PATENT DOCUMENTS

| | | | |
|---|---|---|---|
| 5,693,621 | 12/1997 | Toepfer et al. | 514/25 |
| 5,817,289 | 10/1998 | Klaveness et al. | 424/1.11 |
| 5,834,002 | 11/1998 | Athanikar | 424/440 |

*Primary Examiner*—Jose' G. Dees
*Assistant Examiner*—Dameron Jones
*Attorney, Agent, or Firm*—D. J. Perrella

[57] ABSTRACT

An object of the present invention is to provide a non-invasive method to detect *H. pylori* within the stomach and duodenum. Another object is to provide a non-invasive method to localize this organism within the stomach and duodenum. A further object is to provide a kit containing the reagents for carrying out the diagnostic assay of the present invention.

11 Claims, No Drawings

DIAGNOSTIC ASSAY FOR LOCALIZING H. PYLORI

BACKGROUND OF THE INVENTION

In the United States alone, twenty-five million persons suffer from peptic ulcers, four million of them chronically. Approximately one million victims are hospitalized annually. The major etiologic agent of gastritis and peptic ulcers is Helicobacter pylori (H. pylori).

While several methods to detect H. pylori infection are known, all suffer from one or more drawbacks. Serological detection of antibodies against H. pylori is routinely employed. Unfortunately, the antibody continues to be present even after eradication of the organism. A breath test, involving the consumption of radioactive carbon has been approved, but only detects the presence of the organism. Endoscopy followed by biopsy is another method to detect and to some extent localize Helicobacter, but this is a serious invasive procedure. A non-invasive method to localize H. pylori within the stomach and duodenum does not exist. The ability to localize H. pylori within the upper gastrointestinal tract would be an important component of the clinician's treatment protocol, enables, for example, non-invasive observation of the course of therapy.

OBJECTS OF THE INVENTION

It is, accordingly, an object of the present invention to provide a non-invasive method to detect H. pylori within the stomach and duodenum. Another object is to provide a non-invasive method to localize this organism within the stomach and duodenum. A further object is to provide a kit containing the reagents for carrying out the diagnostic assay of the present invention. These and other objects of the present invention will be apparent from the following description.

DETAILED DESCRIPTION

The present invention is based upon the ability of H. pylori to create an area of elevated pH (alkaline conditions) within the acidic milieu of the stomach by generating ammonia from urea through the action of its powerful enzyme, urease. Alkaline pH also favors the precipitation of a calcium phosphate compound, e.g., calcium phosphate itself or one more of its transformed products, such as, e.g. hydroxyapatite. Because the distribution of H. pylori is usually "patchy", that is to say, discontinuous, precipitation can be anticipated to be localized and not diffuse. The following ingredients are ingested orally at intervals of about 5 to about 45 minutes in carrying out the method of the present invention: (1) a dilute solution of a pharmaceutically acceptable acidulant (if desired, the solution may be sweetened with saccharin or another sweetener), (2) a salt of a pharmaceutically acceptable divalent cation and a pharmaceutically acceptable anion, (3) optionally urea, (4) another dilute solution of a pharmaceutically acceptable acidulant (if desired, the solution may be sweetened with saccharin or another sweetener), and (5) a pharmaceutically acceptable imaging agent.

The urease of H. pylori, which splits urea to generate ammonia, results in the formation of an alkaline pH in localized areas of H. pylori infection and the crystallization of a divalent cation salt. Then the imaging agent becomes bound to the divalent cation due to the attraction between the anionic moiety of the technetium-99 conjugate, and subsequent imaging of the bound technetium compound by appropriate means reveals the localized area(s) of H. pylori infection.

The solution of pharmaceutically acceptable acidulant used in the first and fourth steps typically contains from about 50 ml to about 300 ml of a dilute solution of the acidulant, e.g. from about 0.05 Normal to about 0.15N, and preferably about 0.1N. This solution, typically in a quantity of about 25 mg. The acidulant can be any pharmaceutically acceptable acidulant, for example, adipic acid, ascorbic acid, citric acid or fumaric acid.

The pharmaceutically acceptable divalent cation is, for example, Ba, Bi, Ca, Cu, Mg, Ni, Sr or Zn. Examples of the pharmaceutically acceptable anion are, without intending to be limited therto, bisphosphonate, carbonate, citrate, galate, pyrophosphate, phosphate, subcarbonate, subsalicylate, or tartrate. As examples of suitable salts there may be mentioned $CaCO_3$ $CaHPO_4$, $Ca(OH)(PO_4)3$, $MgNH_4PO_4 \cdot 6H_2O$ (struvite), $Ca_{10}(PO_4)_6CO_3$ (carbonate apatite), (or transformed forms of such salts, such as hydroxyapatite), $BiHPO4$, bismuth citrate, bismuth subcarbonate, bismuth subcitrate, and colloidal forms thereof, bismuth subgalate, bismuth salicylate, bismuth subsalicylate, bismuth tartrate and tripotassium dicitrato bismuthate. Because these salts usually have low solubility in water, it is generally desirable to dissolve them in a dilute solution of a physiologically acceptable acid. While the amount of the salt of the divalent cation is not critical, it is generally employed in an amount of from about 5 mg to about 10 g, preferably from about 10 mg to about 7.5 g, and most preferably from about 50 mg to about 5 g.

The urea is administered to insure the presence of a substrate for the enzyme urease. Where sufficient endogenous urea is present, no urea need be administrated. The urea is administrated in either solid or liquid form, preferably, in the form of an aqueous solution containing from about 30 to about 70 mg of urea per 100 ml of water, and most preferably, about 50 mg of urea per 100 ml of water.

The imaging agent is a pharmaceutically acceptable radioactive isotope conjugated with a phosphate-containing anion. An example of such an imaging agent is the radioactive metal, technetium-99, which is routinely detected in the clinical setting with a gamma camera. The technetium-99 imaging agent is preferably conjugated to a bisphosphonate, carbonate, citrate, pyrophosphate, phosphate, subcarbonate, subsalicylate, or tartrate anion, or to hexaglutamic acid. The quantity of the imaging agent that is used corresponds to the supplier's directions.

The present invention, therefore, comprises a method for detecting areas of H. pylori infection by oral administration of an acidulant, a salt of a pharmaceutically acceptable divalent cation and a pharmaceutically acceptable anion, optionally urea, additional acidulant, and a radioactive imaging agent.

The following examples illustrate the present invention without, however, limiting the same thereto.

EXAMPLE 1

A patient diagnosed with an ulcer of the upper GI tract is administrated 200 ml of 0.1N citric acid flavored with 25 mg of saccharin. After 15 minutes the patient is administrated 2 g of $CaHPO_4$ in 100 ml of 0.1N citric acid. After 15 minutes 200 ml of 0.1N citric acid is administrated, followed after another period of 15 minutes by the technetium-99 bisphosphonate imaging agent. After a few minutes the stomach is examined by means of a gamma camera whereby localized areas of H. pylori infection are disclosed and located

EXAMPLE 2

Another patient diagnosed with an ulcer of the upper GI tract is administrated 150 ml of 0.15N citric acid containing 5 g of Ca(OH)(PO$_4$)$_3$. After 35 minutes 100 ml of water containing 50 mg of urea is administrated, followed by 300 ml of 0.05N citric acid, and after a further 25 minutes by the technetium-99 phosphonate imaging agent. After a few minutes the stomach is examined by means of a gamma camera whereby localized areas of *H. pylori* infection are disclosed and located.

EXAMPLE 3

The procedure of Example 1 is repeated with another patient except that the pharmaceutically acceptable salt is bismuth citrate.

EXAMPLE 4 the procedure of Example 1 is repeated with another patient except that the pharmaceutically acceptable salt is CaCO$_3$.

What is claimed is:

1. A method of detecting areas of suspected *H. pylori* infection in the upper GI tract comprising administering to a patient having, or suspected of having, *H. pylori* infection a dilute solution of a pharmaceutically acceptable acidulant, a pharmaceutically acceptable salt of a pharmaceutically acceptable divalent cation and a pharmaceutically acceptable anion, optionally a dilute solution of urea, a second dilute solution of a pharmaceutically acceptable acidulant, and a pharmaceutically acceptable imaging agent capable of binding to the divalent cation.

2. The method of claim 1 wherein the acidulant is adipic acid, ascorbic acid, citric acid or fumaric acid, the divalent cation of the pharmaceutically acceptable salt is Ba, Bi, Ca, Cu, Mg, Ni, Sr or Zn, the anion of the pharmaceutically acceptable salt is phosphonate, bisphosphonate or phosphate, and the imaging agent is a pharmaceutically acceptable radioactive isotope conjugated with a phosphate-containing anion.

3. The method of claim 2 wherein the acidulant has a normality of from about 0.05N to about 0.15N, the pharmaceutically acceptable salt is administered in a quanity of from about 5 g to about 10 g, and the pharmaceutically acceptable radioactive isotope is conjugated to a phosphate, phosphonate, or bisphosphonate anion.

4. The method of claim 3 wherein urea is added in a quantity of from about 30 mg to about 70 mg.

5. The method of claim 1 wherein the areas of *H. pylori* infection are detected by means of an ionization detector.

6. The method of claim 5 wherein the ionization detector is a gamma camera.

7. The method of claim 2 wherein the radioactive isotope is technetium-99.

8. A kit containing the reagents for carrying out the method of claim 1 having therein at least a single unit dosage amount of each of a dilute solution a pharmaceutically acceptable acidulant, a pharmaceutically acceptable salt of a pharmaceutically acceptable divalent cation and a pharmaceutically acceptable anion, optionally a dilute solution of urea, a second dilute solution of a pharmaceutically acceptable acidulant, and a pharmaceutically acceptable imaging agent capable of binding to the divalent cation.

9. A kit according to claim 8 wherein the optional urea is present.

10. A composition for detecting areas of *H. pylori* infection in the upper GI tract comprising detectably effective amounts of the following ingredients: a pharmaceutically acceptable acidulant, a pharmaceutically acceptable salt of a pharmaceutically acceptable divalent cation and a pharmaceutically acceptable anion, a second dilute solution of a pharmaceutically acceptable acidulant, and a pharmaceutically acceptable imaging agent capable of binding to the divalent cation.

11. The composition of claim 10 additionally containing a detectably effective amount of urea.

* * * * *